(12) United States Patent
Jun et al.

(10) Patent No.: US 9,754,848 B2
(45) Date of Patent: Sep. 5, 2017

(54) GAS SENSOR PACKAGE

(71) Applicant: LG INNOTEK CO., LTD., Seoul (KR)

(72) Inventors: Sung Gon Jun, Seoul (KR); Jee Heum Paik, Seoul (KR); Ji Hun Hwang, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 110 days.

(21) Appl. No.: 14/595,546

(22) Filed: Jan. 13, 2015

(65) Prior Publication Data
US 2015/0198551 A1 Jul. 16, 2015

(30) Foreign Application Priority Data

Jan. 14, 2014 (KR) .................. 10-2014-0004512
Mar. 25, 2014 (KR) .................. 10-2014-0034573

(51) Int. Cl.
| | | |
|---|---|---|
| *G01N 27/26* | (2006.01) | |
| *H01L 23/10* | (2006.01) | |
| *H01L 23/057* | (2006.01) | |
| *G01N 27/12* | (2006.01) | |

(52) U.S. Cl.
CPC ............ *H01L 23/10* (2013.01); *H01L 23/057* (2013.01); *G01N 27/128* (2013.01); *H01L 2224/16225* (2013.01); *H01L 2924/0002* (2013.01)

(58) Field of Classification Search
CPC .................. G01N 27/404–27/4045; G01N 27/02–27/028; G01N 27/04–27/205; G01N 27/22–27/24; G01N 2027/02; G01N 2027/22; G01N 33/0004; G01N 33/0009; G01N 33/0027
USPC ............. 204/431–432, 415; 73/23.31, 31.05, 73/31.06
See application file for complete search history.

(56) References Cited

U.S. PATENT DOCUMENTS

| | | | | |
|---|---|---|---|---|
| 4,812,221 A | * | 3/1989 | Madou | ............... G01N 27/4045 204/412 |
| 6,140,144 A | * | 10/2000 | Najafi | ................ B81C 1/00269 438/106 |
| 2001/0040248 A1 | * | 11/2001 | Toyoda | ................... H01L 29/84 257/254 |
| 2007/0292957 A1 | * | 12/2007 | Chua | ................. G01N 15/0826 436/5 |
| 2015/0090002 A1 | * | 4/2015 | Paik | ..................... B81B 7/0061 73/31.06 |

FOREIGN PATENT DOCUMENTS

JP 201298234 * 5/2012

* cited by examiner

*Primary Examiner* — Bach Dinh
(74) *Attorney, Agent, or Firm* — KED & Associates, LLP

(57) ABSTRACT

Provided is a gas sensor package, including: a gas sensing element; and a substrate on which the gas sensing element is disposed, in which a through hole corresponding to the gas sensing element is formed.

12 Claims, 6 Drawing Sheets

GAS SENSOR PACKAGE

CROSS-REFERENCE TO RELATED APPLICATIONS

This application claims priority under 35 U.S.C. §119 to Korean Application No. 10-2014-0004512, filed on Jan. 14, 2014 and Korean Patent Application No. 10-2014-0034573, filed on Mar. 25, 2014, in the Korean Intellectual Property Office, whose entire disclosures are hereby incorporated by reference.

BACKGROUND

1. Field

Embodiments of the present disclosure relate to a gas sensor package.

2. Background

With regard to requirements for a gas sensor, the gas sensor is needed to have characteristics, such as speed showing how fast the gas sensor can respond to a situation, sensibility which can respond to the detection of gas in spite of the detection of a small amount of the gas, durability showing how long the gas sensor can operate, economic efficiency showing that the sensor can be used by consumers without a financial burden, and the like.

Also, in order for the gas sensor to be combined with an existing semiconductor process technology, the gas sensor should have characteristics of the easiness of integration and enumeration. A home gas leakage alarm made of tin oxide ($SnO_2$) as a material and the like come into wide use as a practical gas sensor.

The gas sensor is divided into a semiconductor type using a change of resistance values according to a change in the amount of gas and an oscillator type using a change in an oscillation frequency generated when gas is absorbed onto an oscillator that oscillates with a predetermined frequency. Most of the gas sensors have been used as the semiconductor type gas sensors having simple circuits and showing a stable thermal property at room temperature.

However, with regard to a configuration of the conventional gas sensor in which a gas sensor element is mounted on a substrate using a soldering process, it is problematic in that chips are separated or a location of the chips is distorted during a manufacturing process due to vibrations generated upon handling because adhesive strength is reduced upon mounting the chips using the soldering process. Furthermore, since the configuration has a structure in which the gas sensor element is exposed to the substrate, it is problematic in that the gas sensor element is damaged by an external impact.

BRIEF DESCRIPTION OF THE DRAWINGS

The embodiments will be described in detail with reference to the following drawings in which like reference numerals refer to like elements wherein.

DETAILED DESCRIPTION

Figure 1:
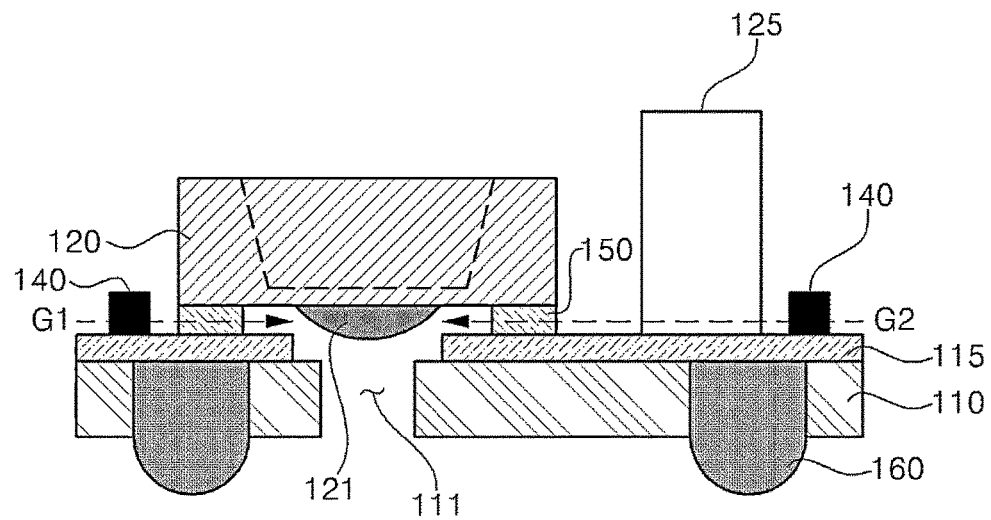
FIGS. 1 to 4 are views illustrated for explaining a manufacturing method and a configuration of a gas sensor package according to an embodiment of the present disclosure.

Hereinafter, the configurations and operations according to embodiments of the present disclosure will be described in detail with reference to the accompanying drawings. The present disclosure may, however, be embodied in different forms and should not be construed as limited to the embodiments set forth herein. In the explanation with reference to the accompanying drawings, regardless of reference numerals of the drawings, like numbers refer to like elements through the specification, and repeated explanation thereon is omitted. Terms such as a first term and a second term may be used for explaining various constitutive elements, but the constitutive elements should not be limited to these terms. These terms are only used for the purpose for distinguishing a constitutive element from other constitutive element. As used herein, the singular forms "a," "an" and "the" are intended to include the plural forms as well, unless the context clearly indicates otherwise.

FIGS. 1 to 4 are views illustrated for explaining a manufacturing method and a configuration of a gas sensor package according to an embodiment of the present disclosure.

A method of manufacturing a gas sensor package according to an embodiment of the present disclosure will be described with reference to FIGS. 1 to 4.

Figure 2:
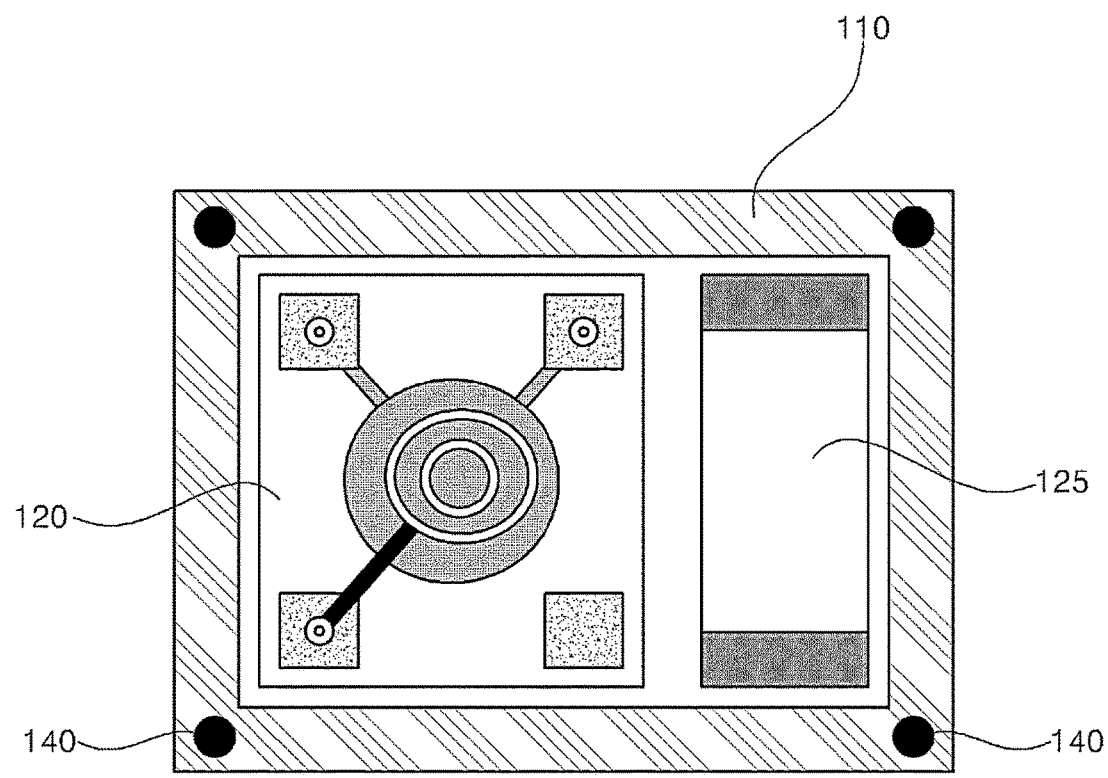

As illustrated in FIGS. 1 and 2, a gas sensing element 120 is formed on a substrate 110.

At this time, the gas sensing element 120 may be mounted by a conductive material layer 150 of the substrate using a flip chip bonding method. More specifically, the substrate 110 includes a metal pattern layer 115 made of a metal material and the gas sensing element 120 is mounted to the metal pattern layer 115.

At this time, a through hole 111 serving as the path of gas may be formed in the substrate 110.

Also, the gas sensor package according to the present embodiment of the disclosure may include gas moving path parts G1, G2 serving as the movement paths of gas and may facilitate the inflow of gas via the gas moving path pats G1, G2.

As illustrated in FIGS. 1 and 2, a gas sensing part 121 of the gas sensor element 120 may be aligned to correspond to the through hole 111 of the substrate 110 that may come into contact with the gas.

Moreover, by forming a metal filling part 160 protruding to a lower portion of the substrate 110, the substrate 110 made of a metal material may facilitate the inflow and movement of gas via separation with the other structures such as a printed circuit board and the like arranged at the lower portion, thereby functioning to increase gas sensing efficiency.

Meanwhile, in FIGS. 1 and 2, even though the gas moving path parts G1, G2 are illustrated as if each path arranged to the gas sensing element 120 is blocked, these drawings show one cross-sectional view. Thus, since the conductive material layer 150 is only formed at one portion of the substrate, the gas moving path parts may be uniformly formed along an edge around the gas sensing element 120.

The gas sensing element 120 include a gas sensing part 121 for enabling gas sensing. Structures of all gas sensing modes, which have been commonly commercialized, may be applied to the gas sensing part 121. A sensing element using an oxide semiconductor, a sensing element using a carbon nanotube, various other sensing semiconductor chip, or the like may be applied to the gas sensing part.

Also, according to the present embodiment of the disclosure, the gas sensor package may further include an output change part 125 as well as the gas sensing element on the substrate 110. The output change part 125 may be also mounted by the conductor material layer 150 using a flip chip bonding method.

The output change part 125 may be composed of a passive element for converting a resistance type output into a voltage type output. A fixed resistance or negative temperature coefficient (NTC) thermistor electrically connected to the metal pattern and the gas sensing element may be used as the passive element.

The output change part 125 converts the resistance output mode of the gas sensing element 120 into the voltage output mode so that the gas sensing element can be applied to various IT devices (including a smart phone or the like). That is, a fixed resistance or NTC thermistor is attached to the side of an end of the gas sensing element 120 so that the resistance type output can be converted into the voltage type output.

Figure 3:
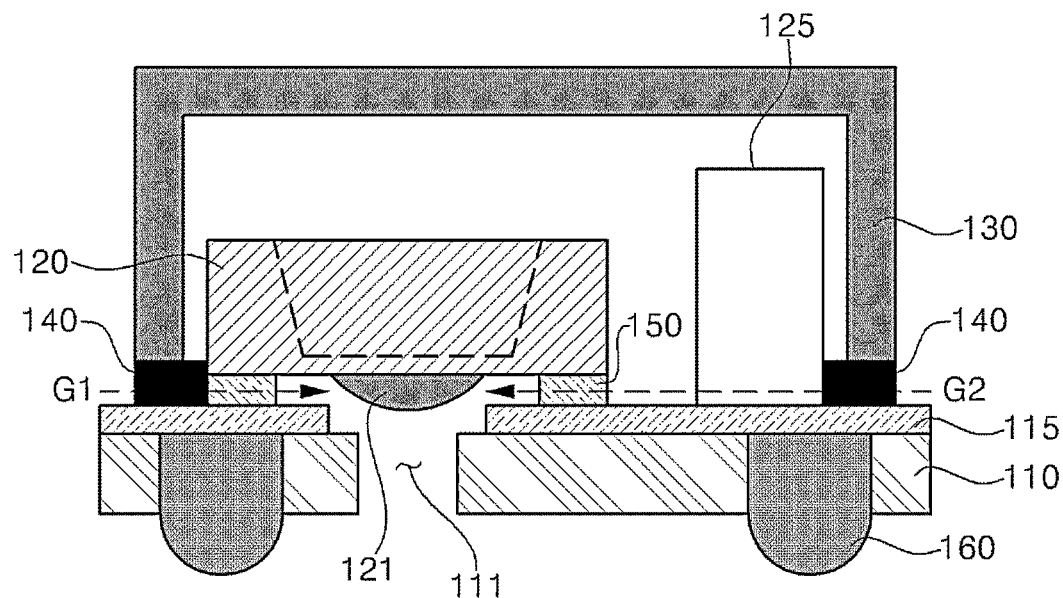
Figure 4:
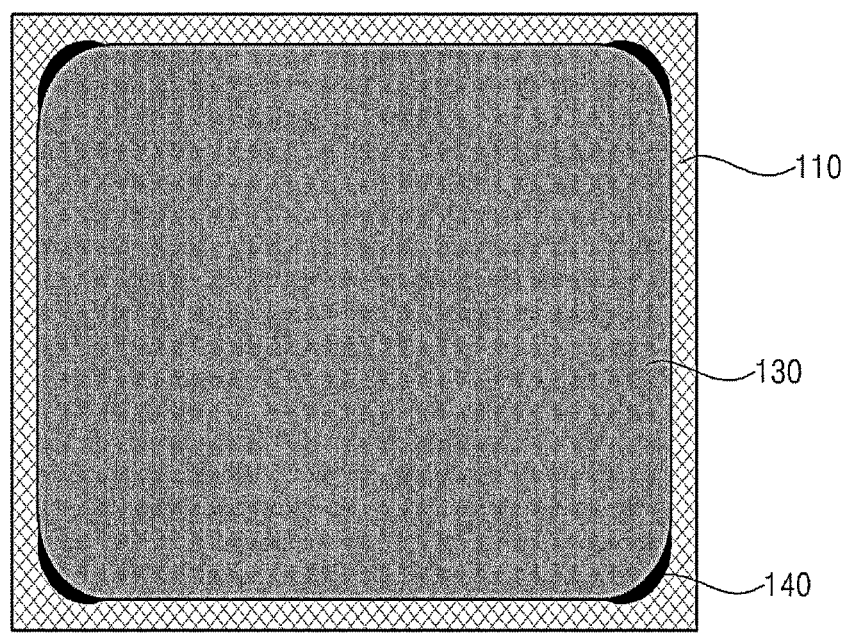

An adhesive part 140 may be coated around the gas sensing element 120 and the output change part 125. At this time, the adhesive part 140 may be made of an epoxy material Then, as illustrated in FIGS. 3 and 4, a protective cap 130 enables the adhesive part 140 to be diffused by applying pressure to the adhesive part 140 so that the adhesive part 140 can be formed to come into contact with at least one portion of the gas sensing element 120.

At this time, the adhesive part 140 may be also formed to come into contact with the conductive material layer 150 as well as the gas sensing element 120.

Like the present embodiment of the present disclosure, when pressure is applied to the adhesive part 140 by the protective cap 130, the protective cap 130 may be stably installed by only an installation process of the protective cap 130 without performing a process for precisely coating the adhesive part 140 so that a defect rate generated during a production process can be reduced and a production cost can be reduced by simplifying the process.

Also, as the gas sensing element 120 is additionally fixed using the adhesive part 140 after the gas sensing element has been mounted using the conductive material layer 150, adhesive strength between the substrate 110 and the gas sensing element 120 can be further strengthened.

Figure 5:
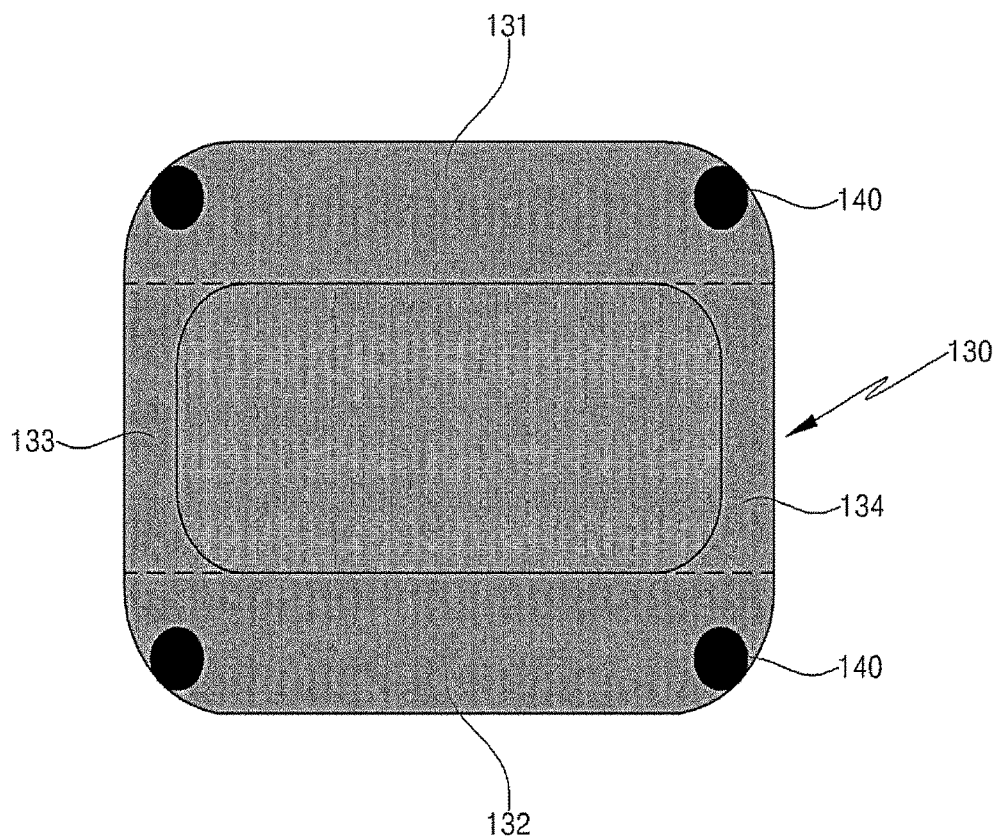
FIG. 5 is a view indicating a corresponding position of the adhesive part from the protective cap according to the embodiment of the present disclosure.

FIG. 5 is a view indicating a corresponding position of the adhesive part from the protective cap according to the embodiment of the present disclosure and illustrates a surface of the protective cap toward the substrate.

The configuration of the gas sensor package according to an embodiment of the present disclosure will be hereinafter described with reference to FIGS. 3 to 5.

As illustrated in FIGS. 3 and 4, the gas sensor package according to the present embodiment of the disclosure includes: the substrate 110; the gas sensing element 120, the protective cap; and the adhesive part 140. Also, the gas sensor package according to the present embodiment of the disclosure may further include the output change part 125.

The gas sensing element 120 is formed on the substrate 110, and the gas sensing element 120 performs gas sensing. More specifically, the substrate 110 includes the metal pattern layer 115 made of a metal material. The gas sensing element 120 is mounted to the metal pattern layer 115, and the through hole 111 is formed in the substrate 110 so as to serve as a path of gas to the gas sensing element 120.

As shown in FIGS. 3 and 4, when a bonding wire is removed by directly bonding the gas sensing element 120 to the substrate 110 using a flip chip bonding method, the gas sensor package can be further miniaturized and a production cost can be also reduced.

Also, the gas sensor package according to the present embodiment of the disclosure may further include gas moving path parts G1, G2 serving a movement path of gas and may facilitate the inflow of gas via the gas moving path parts G1, G2.

As illustrated in FIGS. 3 and 4, the gas sensing part 121 of the gas sensing element 120 may be aligned to correspond to the through hole 111 of the substrate 110 that can come into contact with gas according to movement of the gas of the outside. In term of sensing efficiency, it is the most efficient to form a structure in which the gas sensing part 110 is exposed via the through hole 111 in order to increase contact efficiency with the gas, namely, it is the most efficient to arrange the gas sensing part 121 and the through hole 111 so that the centers thereof can be aligned. Of course, the present disclosure is not limited thereto, with regard to the align configuration, the gas sensing part 121 and the through hole 111 may be arranged to deviate from each other within a predetermined range. In such a case, in the present embodiment of the disclosure, gas detection may be complementarily performed via the gas moving path parts G1, G2 from a side of the gas sensing element 120 so that an effect of the improvement of sensing efficiency can be equally implemented.

Moreover, the substrate 110 made of a metal material may include the metal filling part 160 formed to protrude to a lower portion of the substrate 110. The metal filling part 160 may facilitate the inflow and movement of gas via separation with the other structures such as a printed circuit board and the like arranged to the lower portion and may function to increase gas sensing efficiency.

Meanwhile, in FIGS. 3 and 4, even though the gas moving path parts G1, G2 show as if each path arranged to the gas sensing element 120 is blocked, these drawings show one cross-sectional view. Thus, since the conductive material layer 150 is only formed at one portion of the substrate, the separation spaces may be uniformly formed along an edge around the gas sensing element 120.

Specifically, the metal pattern layer 115 of an upper surface of the substrate 110 may be directly adhered to an electrode of the gas sensing element 120 and may be formed in a structure in which a surface treated plating layer such as Ag, Au, Sn and the like is included in a Cu layer, thereby enabling the improvement of adhesive strength with the electrode of the gas sensing element 120. In particular, the metal pattern layer 115 is formed to have a thickness ranging from 1 μm to hundreds of μm so as to function to implement the gas moving path parts G1, G2 that enable the ventilation of gas to a side portion of the gas sensing element 120.

Also, the gas sensing element 120 includes the gas sensing part 121 for enabling gas sensing, and structures of all gas sensing modes, which have been commonly commercialized, may be applied as the gas sensing part 121. A sensing element using an oxide semiconductor, a sensing element using a carbon nanotube, various other sensing semiconductor chip, or the like may be applied to the gas sensing part.

The protective cap 130 may be made of a metal material to cover the gas sensing element 120.

The protective cap 130 is an element intended for protecting the gas sensing element 120 and is adhered to the substrate via the adhesive part 140.

At this time, the adhesive part 140 according to the present embodiment of the disclosure is made of epoxy so as to come into contact with at least one portion of the gas sensing element 120.

More specifically, the adhesive part 140 may be coated around the gas sensing element 120 from the substrate 110, and the protective cap 130 may enable the adhesive part 140 to be diffused by applying pressure to the adhesive part 140.

Thus, the adhesive part 140 is formed to come into contact with the gas sensing element 120.

At this time, FIG. 5 illustrates a surface of the protective cap 130 toward the substrate 110.

As illustrated in FIG. 5, the protective cap 130 may be configured such that the surface toward the substrate is divided into a plurality of areas 131, 132, 133, 134, and a width of any one area of the plurality of areas 131, 132, 133, 134 is formed wider than each width of the remaining areas.

For example, in the protective cap 130, each width of the first area 131 and the second area 132 may be formed wider than each width of the remaining areas 133, 134, and the adhesive part 140 may be formed in the first area 131 and the second area, which have been more widely formed, respectively.

Accordingly, as shown in FIG. 3, the adhesive part 140 is coated around the gas sensing element 120 on the substrate 110, and the protective cap enables the adhesive part 140 to be diffused by applying pressure to the adhesive part so that the adhesive part can come into contact with the gas sensing element 120.

As illustrated in FIG. 3, the gas sensing element 120 may be mounted to the substrate via the conductive material layer 150 using a flip chip bonding method, and the adhesive part 140 may be formed to come into contact with the conductive material layer 150 as well as the gas sensing element 120.

Like the present embodiment of the present disclosure, when pressure is applied to the adhesive part 140 by the protective cap 130, the protective cap 130 may be stably installed by only an installation process of the protective cap 130 without performing a process for precisely coating the adhesive part 140 so that a defect rate generated during a production process can be reduced and a production cost can be reduced by simplifying the process.

Also, as the gas sensing element 120 is additionally fixed using the adhesive part 140 after the gas sensing element has been mounted using the conductive material layer 150, adhesive strength between the substrate 110 and the gas sensing element 120 can be further strengthened.

Furthermore, as shown in FIG. 3, when a bonding wire is removed by directly bonding the gas sensing element 120 to the substrate 110 using a flip chip bonding method, the gas sensor package can be further miniaturized and a production cost can be also reduced.

Meanwhile, the gas sensing element 120 may be configured such that the plurality of gas sensing elements is formed on the substrate 120.

Also, according to the present embodiment of the disclosure, the gas sensor package may further include the output change part 125 as well as the gas sensing element 120 on the substrate 110.

The output change part 125 is electrically connected to the gas sensing element 120, thereby changing an output mode of the gas sensing element.

The output change part 125 may be composed of a passive element for converting a resistance type output into a voltage type output. A fixed resistance or negative temperature coefficient (NTC) thermistor electrically connected to the metal pattern and the gas sensing element may be used as the passive element.

The output change part 125 converts the resistance output mode of the gas sensing element 120 into the voltage output mode so that the gas sensing element can be applied to various IT devices (including a smart phone or the like). That is, a fixed resistance or NTC thermistor is attached to the side of an end of the gas sensing element 120 so that the resistance type output can be converted into the voltage type output.

In such a case, when the negative temperature coefficient thermistor is connected to the side of an end of the gas sensing element, it is advantageous in that a regular initial voltage value can be obtained by compensating an initial sensing material for a resistance change value.

That is, in a case where a fixed resistance or NTC thermistor is used at the outside of a printed circuit board, it is problematic in that the size of an entire module is increased, and a separate circuit design should be performed. However, as a package including the output change part intended for converting an output of the gas sensor into a voltage mode is implemented, the miniaturized gas sensor may be provided. Furthermore, with regard to a resistance change value for each temperature of an NTC thermistor, an NTC thermistor having the same ratio as that of a resistance curve of a sensing material is adopted so that temperature compensation can be performed, thereby enabling the compensation of initial resistance resulting from a temperature change of the sensing material.

Like the gas sensing element 120, the output change part 125 configured as described above may be formed on the substrate 110, and the output change part 125 may be covered by the protective cap 130.

Also, like the gas sensing element 120, the adhesive part 140 may be formed to come into contact with the output change part 125, and the adhesive part 140 may be coated around the output change part 125 from the substrate 110. The protective cap 130 may enable the adhesive part 140 to be diffused by applying pressure to the adhesive part 140 so that the adhesive part can be formed to come into contact with the output change part 125.

Like the gas sensing element 120, the output change part 125 may be mounted to the substrate via the conductive material layer 150 using a flip chip bonding method, and the adhesive part 140 may be formed to come into contact with the conductive material layer 150 as well as the output change part 125.

Accordingly, the output change part 125 is additionally fixed using the adhesive part 140 after the output change part has been mounted using the conductive material layer 150 so that adhesive strength between the substrate 110 and the output change part 125 can be further strengthened. Furthermore, the output change part 125 is directly adhered to the substrate 110 using the flip chip bonding method so that the gas sensor package can be further miniaturized.

Figure 6:
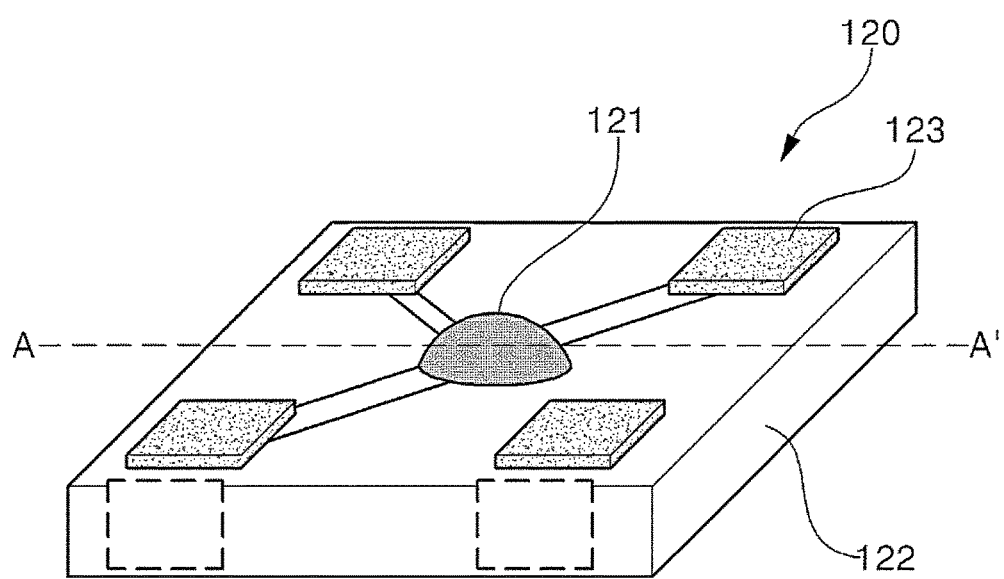
FIGS. 6 to 8 are views illustrating a gas sensing element according to an embodiment of the present disclosure.
Figure 7:
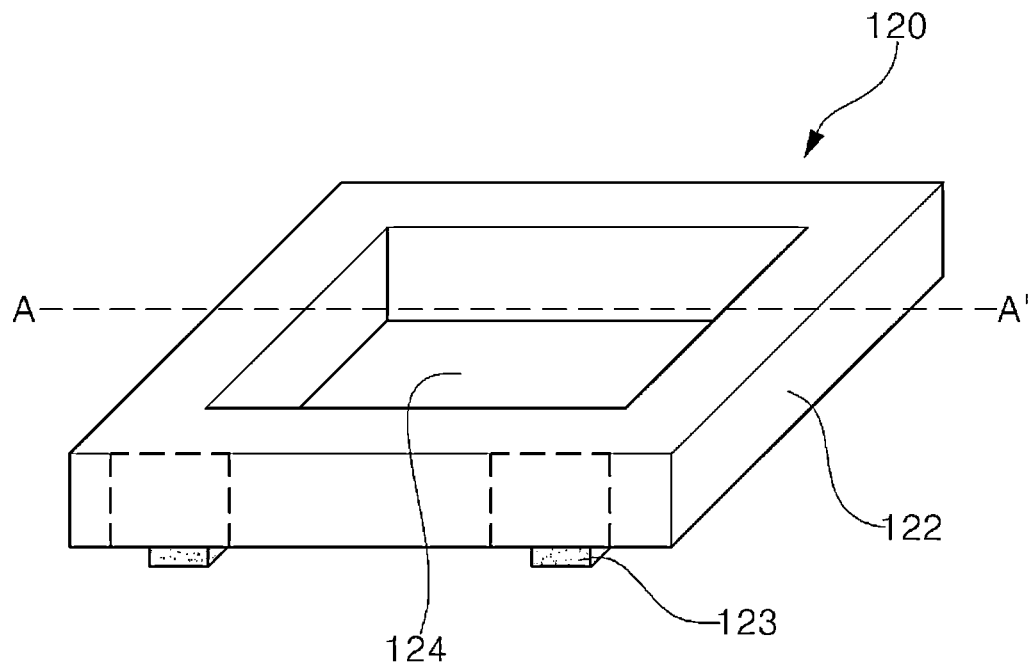
Figure 8:
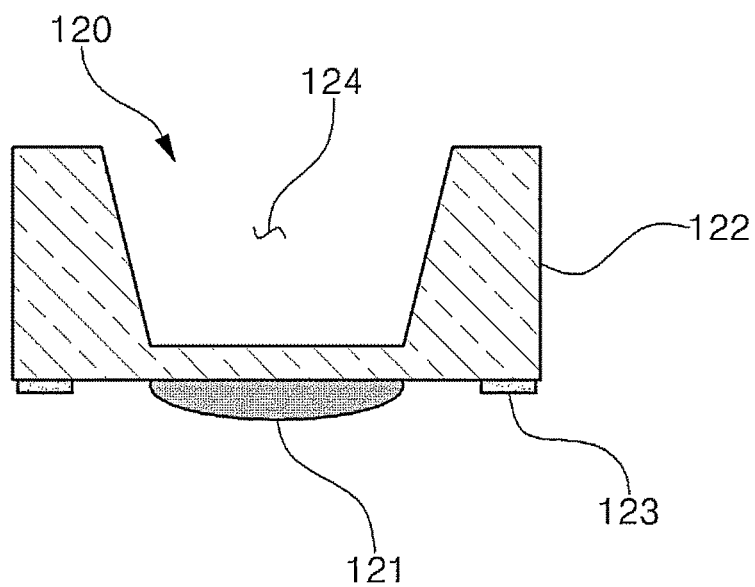

FIGS. 6 to 8 are views illustrating a gas sensing element according to an embodiment of the present disclosure.

More specifically, FIG. 6 is a top view of the gas sensing element according to the embodiment of the present disclosure, FIG. 7 is a bottom view of the gas sensing element according to the embodiment of the present disclosure, and FIG. 8 is a cross-sectional view of the gas sensing element according to the embodiment of the present disclosure and illustrates a cross section taken along lines A-A'.

The gas sensing element according to the present embodiment of the disclosure includes a body part 122, a gas sensing part 121 and an electrode 123.

As shown in FIG. 6, the gas sensing part 121 composed of a sensing material or a sensing chip and intended for detecting gas is arranged in the body part 122 and the electrode 123 connectable to an external terminal is provided on an adjacent surface. The gas sensing part and the electrode 123 may be electrically connected to each other. At this time, the gas sensing part 121 may be made of a sensing material having the same resistance change rate for each temperature as that of the output change part 125.

Also, as illustrated in FIG. 7, a cavity 124 is formed inside the body part 122 so that a gas residence time can be secured.

As shown in FIG. 8, the cavity 124 may be formed inside the body part 122 so that a gas residence time can be secured, and the gas sensing part 121 may detect gas entered into the gas sensor package.

Figure 9:
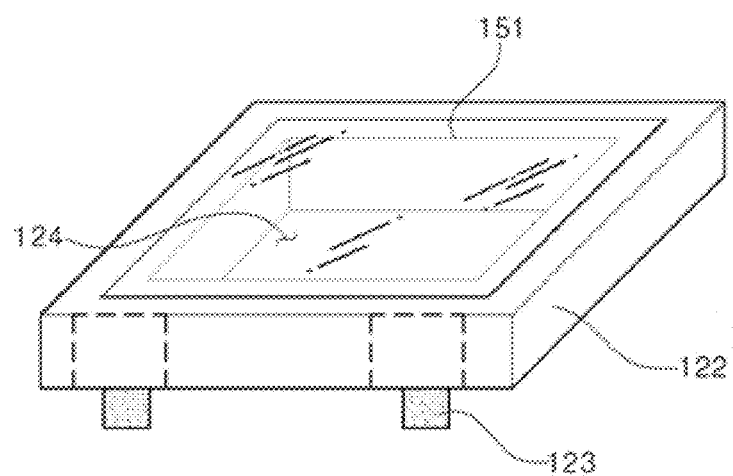
FIGS. 9 and 10 are views illustrating a gas sensing element according to another embodiment of the present disclosure.
Figure 10:
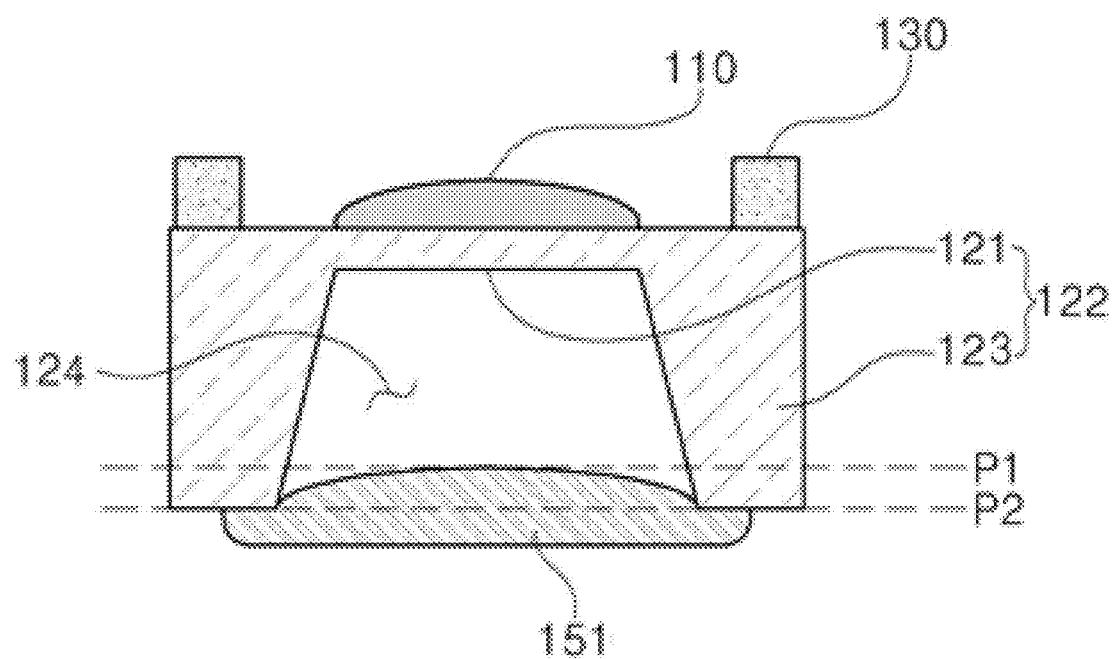

FIGS. 9 and 10 are views illustrating a gas sensing element according to another embodiment of the present disclosure.

As illustrated in FIGS. 9 and 10, the gas sensing element according to another embodiment of the present disclosure may further include the cover member 151 for sealing an upper surface of the cavity 124.

The cover member 151 may be disposed to cover the cavity 124 formed in the body part 122.

The cover member 151 may be formed in a structure in which a separate structure is processed and is adhered with a synthetic resin film such as polyimide and the like, or may be formed in a structure in which sealing is performed by dropping a synthetic resin material having a predetermined viscosity on an upper surface of the cavity using a dispensing method, so that an inner side of the cavity 124 and the gas sensing part 121 can be protected, a space capable of enabling gas for gas sensing to remain can be obtained, and a function of preventing radiant heat can be provided.

In particular, all materials used as a sealant such as a material including epoxy, urethane and Si may be applied as the synthetic resin material. Furthermore, a material having a predetermined viscosity for preventing the material from flowing to an inner portion of the cavity 124 may be used as the synthetic resin material.

Accordingly, as illustrated in FIG. 10, the cover member 151 may be formed to partially further enter to the degree of an inner depth P1 on a side of a lower surface 121 than one surface P2 of a side portion 123 of the body part 122.

As such, the lower surface of the cover member 151 may be implemented to have a curvature according to deflection resulting from gravity of the synthetic resin material having the predetermined viscosity. Thanks to this structure, an upper surface of the cavity 124 has a curvature so that a function of facilitating the stay and circulation of gas can be provided, thereby enabling an increase of sensing sensitivity.

In order to increase sensing efficiency, a minute gas moving hole may be formed in a lower surface of the body part 122. Additionally, a minute gas moving hole may be also formed in a portion of the cover member.

Figure 11:
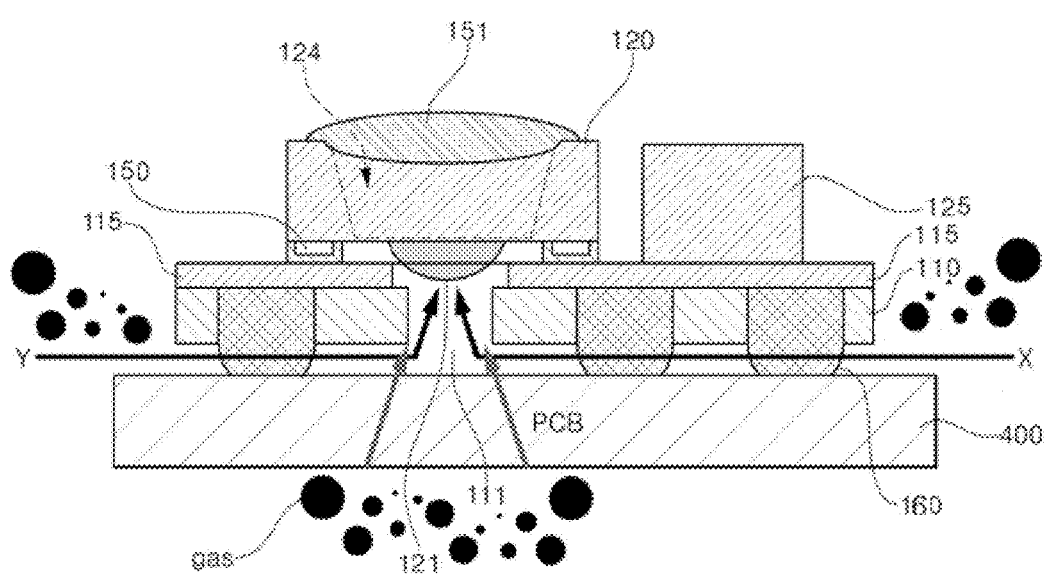
FIG. 11 is a view illustrating a gas sensor package according to another embodiment of the present disclosure.

FIG. 11 is a view illustrating a gas sensor package according to another embodiment of the present disclosure.

The gas sensor package according to another embodiment of the present disclosure may be formed in structure in which the substrate 110 is mounted to a second substrate 400.

The second substrate 400 may be composed a printed circuit board.

At this time, the second substrate 400 may be composed of a printed circuit board made of a flexible material.

According to the present embodiment of the disclosure, the metal filing part 160 of the substrate 110 may be electrically connected to the second substrate 400 which is a printed circuit board.

In particular, the metal filling part 160 protrudes in the direction of a lower surface of the substrate 110 at a predetermined portion to be separated from the substrate by a predetermined distance even after being in contact with the second substrate so that gas moving path parts X, Y can be formed.

In the gas sensor package according to the present embodiment of the disclosure, the gas moving paths X, Y enable the gas sensing part 121 to come into direct contact with gas via the through hole 111 provided in the substrate 110, thereby enabling an increase of sensing efficiency.

The reason why the conventional gas sensors are implemented such that the gas sensing part is disposed to face an upper surface of the substrate is due to an intention for ensuring contact efficiency with gas. Thus, the gas sensing part should be necessarily disposed to face the upper surface, and a protective net having a mesh structure is needed, so a size of the package is necessarily increased.

However, in the gas sensor package according to the embodiment of FIG. 11, a portion which the gas sensing part 121 is provided is mounted to be in contact with a surface of the substrate 110, and thus a separate cap is not installed, thereby enabling miniaturization of the gas sensor package and the reduction of a production cost.

Furthermore, according to the embodiment of FIG. 11, the cavity 124 of the gas sensing element may enable the stay of gas, and the gas moving path parts X, Y for introducing gas from the through hole 111 and a side of the substrate 111 to the gas sensing part 121 may enable the improvement of sensing efficiency.

As set forth above, according to some embodiments of the present disclosure, as pressure is applied to the adhesive part by the protective cap, the protective cap may be stably installed by only an installation process of the protective cap without performing a process for precisely coating the adhesive part so that a defect rate generated during a production process can be reduced and a production cost can be reduced by simplifying the process. Also, according to some embodiments, as the gas sensing element 120 is additionally fixed using the adhesive part 140 after the gas sensing element has been mounted using the conductive material layer 150, adhesive strength between the substrate 110 and the gas sensing element 120 can be further strengthened.

Also, some embodiments of the present disclosure, a bonding wire is removed by directly bonding the gas sensing element 120 to the substrate 110 using a flip chip bonding method so that the gas sensor package can be further miniaturized and a production cost can be also reduced.

Also, according to some embodiments of the present disclosure, a cover member is implemented at an upper surface of an element body so that a cavity can be formed, thereby enabling protection an element including a gas sensing part and implementing the prevention of radiant heat; gas is left in the cavity so that sensing efficiency can be increased; sensing efficiency is increased by enabling inflow of gas and gas sensing via a through hole formed in a first substrate; and a gas sensor having a slimming structure can be formed.

As previously described, in the detailed description of the disclosure, having described the detailed exemplary embodiments of the disclosure, it should be apparent that modifications and variations can be made by persons skilled without deviating from the spirit or scope of the disclosure. Therefore, it is to be understood that the foregoing is illustrative of the present disclosure and is not to be construed as limited to the specific embodiments disclosed, and that modifications to the disclosed embodiments, as well as other embodiments, are intended to be included within the scope of the appended claims and their equivalents.

The present disclosure has been made keeping in mind the above problems. An aspect of embodiments the present disclosure provides a gas sensor package which is configured such that pressure is applied to an adhesive part by a protective cap so that the protective cap can be stably installed by only an installation process of the protective cap without performing a process for precisely coating the adhesive part, thereby reducing a defect rate generated during a production process and a production cost by simplifying the process.

Another aspect of embodiments of the present disclosure provides a gas sensor package which is configured such that a gas sensing element is additionally fixed using an adhesive part after the gas sensing element has been mounted using a conductive material layer so that adhesive strength between a substrate and the gas sensing element can be further strengthened, thereby more firmly fixing the gas sensing element.

Also, a further aspect of embodiments of the present disclosure provides a gas sensor package in which a gas sensing element and a substrate are directly adhered to each other using a flip chip bonding method so that a bonding wire can be removed, thereby reducing a production cost and enabling miniaturization of the gas sensor package.

Also, yet another aspect of embodiments of the present disclosure provides a gas sensor package which is configured such that a cover member is implemented at an upper surface of an element body so that a cavity can be formed, thereby enabling protection an element including a gas sensing part and implementing the prevention of radiant heat; gas is left in the cavity so that sensing efficiency can be increased; sensing efficiency is increased by enabling inflow of gas and gas sensing via a through hole formed in a first substrate; and a gas sensor having a slimming structure can be formed.

According to an aspect of embodiments of the present disclosure, a gas sensor package may include: a gas sensing element; and a substrate on which the gas sensing element is disposed, and in which a through hole corresponding to the gas sensing element is formed.

The gas sensing package may further include: a protective cap for covering the gas sensing element; and an adhesive part that adheres the protective cap to the substrate and comes into contact with at least one portion of the gas sensing element.

The gas sensing package may further include a first gas moving path part formed between the substrate and the protective cap via the adhesive part.

The adhesive part may be disposed around the gas sensing element from the substrate.

The adhesive part may be formed at an edge of a surface toward the substrate of the protective cap.

The adhesive part may contain epoxy.

The protective cap may be configured such that a surface toward the substrate is divided into a plurality of areas and a width of at least one area of the plurality of areas is formed wider than each width of the remaining areas.

The adhesive part may be disposed at a width of any one area that is formed wider than each width of the remaining areas.

The gas sensing element may be mounted by a conductive material layer on the substrate, and the adhesive part may be formed to come into contact with the gas sensing element and the conductive material layer.

The gas sensing element may be formed in plural numbers on the substrate.

The gas sensor package may further include an output change part for converting an output mode of the gas sensing element formed on the substrate.

The output change part may be composed of an NTC (Negative Temperature Coefficient) thermistor or resistance.

The gas sensing element may further include a body part in which a cavity is formed.

The gas sensor package may further include a cover member intended for covering the cavity of the body part.

The gas sensor package may further include a metal filling part formed to protrude from the substrate.

The gas sensor package may further include a second substrate separated from the substrate by the metal filling part.

The gas sensor package may further include a second gas moving path part formed between the substrate and the second substrate by the metal filling part.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A gas sensor package, comprising:
a gas sensing element;
a substrate on which the gas sensing element is arranged, and in which a through hole corresponding to the gas sensing element is formed;
an output change part that converts an output mode of the gas sensing element and is disposed on the substrate;
a protective cap configured to cover the gas sensing element and the output change part;
an adhesive part that adheres the protective cap to the substrate and comes in contact with at least one portion of the gas sensing element and at least one portion of the output change part; and
a first gas moving path formed between the substrate and the protective cap via the adhesive part, wherein the gas sensing element is mounted to the substrate via a conductive material layer, and the adhesive part comes into contact with the conductive material layer, and wherein the gas sensing element is made of a sensing material having same resistance change rate for each temperature as that of the output change part.

2. The gas sensor package of claim 1, wherein the adhesive part is provided around the gas sensing element from the substrate.

3. The gas sensor package of claim 1, wherein the adhesive part is formed at an edge of a surface of the protective cap toward the substrate.

4. The gas sensor package of claim 1, wherein the adhesive part contains epoxy.

5. The gas sensor package of claim 1, wherein the protective cap is configured such that the surface toward the substrate is divided into a plurality of areas, and a width of at least one area of the plurality of areas is formed wider than each width of the remaining areas.

6. The gas sensor package of claim 5, wherein the adhesive part is provided at a width of any one area formed wider than each width of the remaining areas.

7. The gas sensor package of claim 1, wherein multiple gas sensing elements are formed on the substrate.

8. The gas sensor package of claim 1, wherein the output change part is an NTC (Negative Temperature Coefficient) thermistor or resistance.

9. A gas sensor package, comprising:
a gas sensing element having a body in which a cavity, providing a space to hold gas to be sensed, is formed;
a substrate on which the gas sensing element is arranged and in which a through hole corresponding to the gas sensing element is formed; and
a cover configured to cover the cavity of the body of the gas sensing element,
wherein the cover is disposed to partially further enter to a degree of an inner depth on a side of a lower surface than one surface of a side portion of the body, and
wherein the lower surface of the cover has a curvature.

10. The gas sensor package of claim 1, further comprising a metal filling part formed to protrude from the substrate.

11. The gas sensor package of claim 10, further comprising a second substrate separated from the substrate via the metal filling part.

12. The gas sensor package of claim 11, further comprising a second gas moving path formed between the substrate and the second substrate by the metal filling part.

* * * * *